(12) United States Patent
Reddy et al.

(10) Patent No.: US 8,779,143 B2
(45) Date of Patent: Jul. 15, 2014

(54) CRYSTALLINE FORMS OF MARAVIROC PHOSPHATE AND PROCESS FOR MARAVIROC AMORPHOUS FORM

(75) Inventors: Bandi Parthasaradhi Reddy, Hyderabad (IN); Kura Rathnakar Reddy, Hyderabad (IN); Dasari Muralidhara Reddy, Hyderabad (IN); Rapolu Raji Reddy, Hyderabad (IN); Kesireddy Subash Chander Reddy, Hyderabad (IN); Bandi Vamsi Krishna, Hyderabad (IN)

(73) Assignee: Hetero Research Foundation (IN)

( * ) Notice: Subject to any disclaimer, the term of this patent is extended or adjusted under 35 U.S.C. 154(b) by 0 days.

(21) Appl. No.: 13/819,410

(22) PCT Filed: Aug. 30, 2010

(86) PCT No.: PCT/IN2010/000574
§ 371 (c)(1),
(2), (4) Date: Apr. 10, 2013

(87) PCT Pub. No.: WO2012/029067
PCT Pub. Date: Mar. 8, 2012

(65) Prior Publication Data
US 2013/0211091 A1  Aug. 15, 2013

(51) Int. Cl.
*C07D 451/04* (2006.01)

(52) U.S. Cl.
CPC .................................. *C07D 451/04* (2013.01)
USPC .......................................................... 546/125

(58) Field of Classification Search
CPC ..................................................... C07D 451/04
USPC ........................................................... 546/125
See application file for complete search history.

(56) References Cited

U.S. PATENT DOCUMENTS

| 6,667,314 B2 * | 12/2003 | Perros et al. .................. 514/304 |
| 7,576,097 B2 | 8/2009 | Perros et al. |
| 2008/0161264 A1 | 7/2008 | Tung |
| 2008/0280945 A1 | 11/2008 | Lohani et al. |

OTHER PUBLICATIONS

International Search Report and Written Opinion; International Application No. PCT/IN 10/00574; International Filing Date Aug. 30, 2010; Date of Mailing May 2, 2011; 10 pages.

* cited by examiner

*Primary Examiner* — Niloofar Rahmani
(74) *Attorney, Agent, or Firm* — Cantor Colburn LLP

(57) ABSTRACT

The present invention provides novel crystalline forms of maraviroc phosphate, processes for their preparation and pharmaceutical compositions comprising them. The present invention also provides novel process for the preparation of maraviroc amorphous form and pharmaceutical composition comprising it.

24 Claims, 5 Drawing Sheets

CRYSTALLINE FORMS OF MARAVIROC PHOSPHATE AND PROCESS FOR MARAVIROC AMORPHOUS FORM

CROSS-REFERENCE TO RELATED APPLICATIONS

This application is a 371 of PCT/IN2010/000574 filed on Aug. 30, 2010, filed under the provisions of 35 U.S.C. 119 and the International Convention for the protection of Industrial Property, which is incorporated herein by reference.

FIELD OF THE INVENTION

The present invention provides novel crystalline forms of maraviroc phosphate, processes for their preparation and pharmaceutical compositions comprising them. The present invention also provides novel process for the preparation of maraviroc amorphous form and pharmaceutical composition comprising it.

BACKGROUND OF THE INVENTION

Maraviroc and its pharmaceutically acceptable salt or solvate thereof were disclosed in U.S. Pat. No. 6,667,314 (herein after refer to '314 patent). Maraviroc is chemically, N-{(1S)-3-[3-(3-isopropyl-5-methyl-4H-1,2,4-triazol-4-yl)-exo-8-azabicyclo-[3.2.1]oct-8-yl]-1-phenylpropyl}-4,4-difluoro-cyclohexanecarboxamide and has the structural formula:

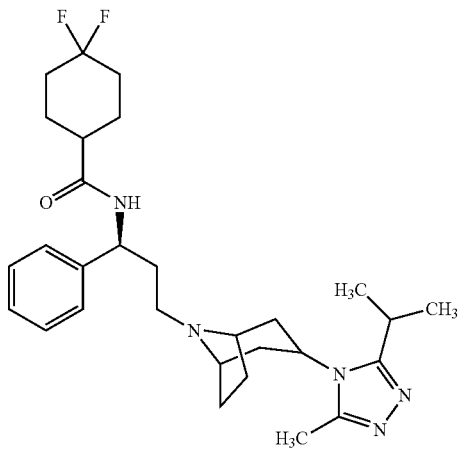 [SMILES: Cc1nnc(C(C)C)n1C1CC2CCC(C1)N2CC[C@H](NC(=O)C1CCC(F)(F)CC1)c1ccccc1]

Maraviroc as modulators of the chemokine receptor CCR5 and thus useful in the treatment of retroviral diseases caused by viruses that utilize CCR5 to enter cells. In particular maraviroc has been disclosed as being a useful therapeutic in the treatment of HIV, a retroviral infection genetically related to HIV, AIDS, or an inflammatory disease.

Polymorphism is defined as "the ability of a substance to exist as two or more crystalline phases that have different arrangement and/or conformations of the molecules in the crystal lattice. Thus, in the strict sense, polymorphs are different crystalline forms of the same pure substance in which the molecules have different arrangements and/or different configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, to dissolution and flow properties of each polymorphic form. Polymorphic forms of a compound can be distinguished in the laboratory by analytical methods such as X-ray diffraction (XRD), Differential Scanning calorimetry (DSC) and Infrared spectrometry (IR).

Solvent medium and mode of crystallization play very important role in obtaining a crystalline form over the other Maraviroc or its salts can exist in different polymorphic forms, which may differ from each other in terms of stability, physical properties, spectral data and methods of preparation.

According to the '314 patent, maraviroc can be prepared by reacting a solution of (1S)-3-[3-(3-isopropyl-5-methyl-4H-1,2,4-triazol-4-yl)-exo-8-azabicyclo[3.2.1]oct-8-yl]-1-phenyl-1-propanamine in methylene chloride and saturated sodium carbonate with a solution of 4,4-difluorocyclohexanecarbonyl chloride in toluene, and isolating to obtain maraviroc.

Crystalline polymorph form A and form B of maraviroc were disclosed in U.S. Pat. No. 7,576,097.

Amorphous form of maraviroc was reported in IP.com Journal (2006), 6(12B), 31. According to this process, amorphous form is obtained from crystalline maraviroc.

Polymorphic forms of maraviroc phosphate are obtained not specifically mentioned in '314 patent. We have discovered novel crystalline forms of maraviroc phosphate.

We have also discovered novel process for the preparation of maraviroc amorphous form. The amorphous form obtained by the process of the present invention is found to have substantially pure as measured by high performance liquid chromatography (HPLC). The process of the invention ensures that amorphous maraviroc can be obtained directly without the need for the preparation of the crystalline maraviroc first, then the conversion of crystalline maraviroc to the maraviroc amorphous form.

Thus, one object of the present invention is to provide a novel crystalline forms of maraviroc phosphate, processes for their preparation and pharmaceutical compositions comprising them.

The crystalline forms of maraviroc phosphate of the present invention may also serve as intermediate for preparation of maraviroc.

Another object of the present invention is to provide a novel process for the preparation of maraviroc amorphous form and pharmaceutical compositions comprising it.

SUMMARY OF THE, INVENTION

In one aspect, the present invention provides a crystalline form of maraviroc phosphate designated as form 1 characterized by peaks in the powder x-ray diffraction spectrum having $2\theta$ angle positions at about 8.4, 9.7, 11.4, 18.2 and 18.8±0.2 degrees.

In another aspect, the present invention provides a process for the preparation of crystalline form 1 of maraviroc phosphate, which comprises:
  a) providing a solution of maraviroc in a ketonic solvent, acetonitrile, an chlorinated solvent or mixture thereof;
  b) adding phosphoric acid to the solution obtained in step (a);
  c) slurrying the reaction mass obtained in step (b); and
  d) isolating crystalline form 1 of maraviroc phosphate.

In another aspect, the present invention provides a pharmaceutical composition comprising crystalline form 1 of maraviroc phosphate and pharmaceutically acceptable excipients.

In another aspect, the present invention provides a crystalline form of maraviroc phosphate designated as form 2 characterized by peaks in the powder x-ray diffraction spectrum having 2θ angle positions at about 9.9, 11.1, 12.5, 14.1, 15.0, 16.0, 17.1, 17.3, 18.0, 20.0 and 23.1±0.2 degrees.

In another aspect, the present invention provides a process for the preparation of crystalline form 2 of maraviroc phosphate, which comprises:
  a) providing a solution of maraviroc in an ester solvent;
  b) adding phosphoric acid to the solution obtained in step (a);
  c) slurrying the reaction mass obtained in step (b); and
  d) isolating crystalline form 2 of maraviroc phosphate.

In another aspect, the present invention provides a pharmaceutical composition comprising crystalline form 2 of maraviroc phosphate and pharmaceutically acceptable excipients.

In another aspect, the present invention provides a crystalline form of maraviroc phosphate designated as form 3 characterized by peaks in the powder x-ray diffraction spectrum having 2θ angle positions at about 3.7, 6.5, 7.5, 9.2, 9.8, 16.4, 18.3, 19.2, 19.8 and 22.6±0.2 degrees.

In another aspect, the present invention provides a process for the preparation of crystalline form 3 of maraviroc phosphate, which comprises:
  a) providing a solution of maraviroc in isopropyl alcohol;
  b) adding phosphoric acid to the solution obtained in step (a);
  c) slurrying the reaction mass obtained in step (b); and
  d) isolating crystalline form 3 of maraviroc phosphate.

In another aspect, the present invention provides a pharmaceutical composition comprising crystalline form 3 of maraviroc phosphate and pharmaceutically acceptable excipients.

In another aspect, the present invention provides a crystalline form of maraviroc phosphate designated as form 4 characterized by peaks in the powder x-ray diffraction spectrum having 2θ angle positions at about 7.2, 9.5, 11.6, 18.4, 18.9, 19.7 and 23.2±0.2 degrees.

In another aspect, the present invention provides a process for the preparation of crystalline form 4 of maraviroc phosphate, which comprises:
  a) providing a solution of maraviroc in ethanol;
  b) adding phosphoric acid to the solution obtained in step (a);
  c) slurrying the reaction mass obtained in step (b) at below 20° C.; and
  d) isolating crystalline form 4 of maraviroc phosphate.

In another aspect, the present invention provides a pharmaceutical composition comprising crystalline form 4 of maraviroc phosphate and pharmaceutically acceptable excipients.

In another aspect, the present invention provides a process for the preparation of maraviroc amorphous form, which comprises:
  a) dissolving an acid addition salt of maraviroc in water;
  b) adjusting the pH of the reaction mass to about 7.0 to 9.0 with a base;
  c) extracting maraviroc into organic solvent;
  d) removing the solvent from the solution obtained in step (c) to obtain a residual mass;
  e) slurrying the residual mass obtained in step (d) with aliphatic hydrocarbon solvent or aromatic solvent; and
  f) isolating maraviroc amorphous form.

Yet another aspect, the present invention provides a pharmaceutical composition comprising maraviroc amorphous form and pharmaceutically acceptable excipients.

X-ray powder diffraction spectrum was measured on a bruker axs D8 advance X-ray powder diffractometer having a copper-Kα radiation. Approximately 1 gm of sample was gently flattered on a sample holder and scanned from 2 to 50 degrees two-theta, at 0.02 degrees to theta per step and a step of 10.6 seconds. The sample was simply placed on the sample holder. The sample was rotated at 30 rpm at a voltage 40 KV and current 35 mA.

DETAILED DESCRIPTION OF THE INVENTION

The term "room temperature" refers to temperature at about 25 to 35° C.

Figure 1:
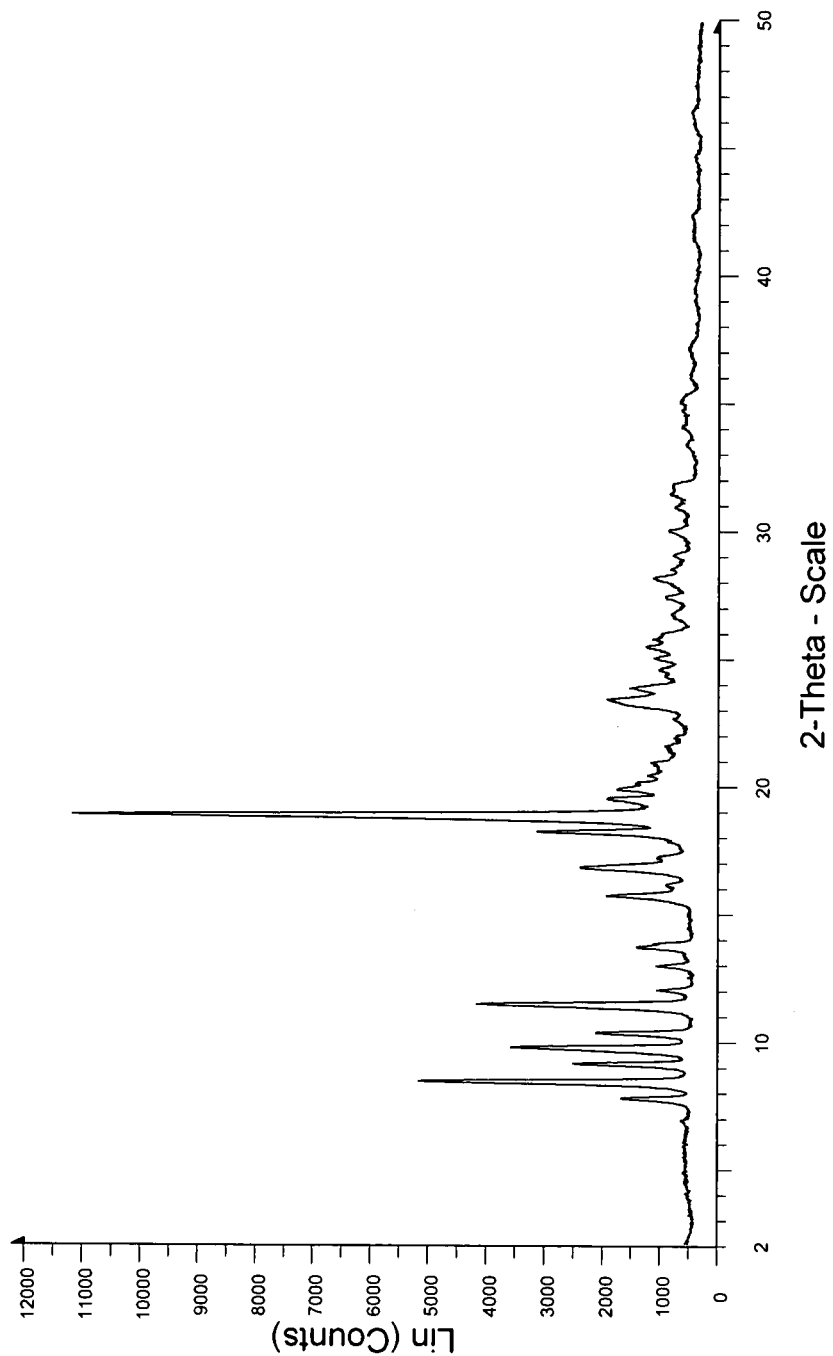
FIG. 1 is X-ray powder diffraction spectrum of crystalline form 1 of maraviroc phosphate.

According to one aspect of the present invention, there is provided a crystalline form of maraviroc phosphate designated as form 1 characterized by peaks in the powder x-ray diffraction spectrum having 2θ angle positions at about 8.4, 9.7, 11.4, 18.2 and 18.8±0.2 degrees. The powdered x-ray diffractogram (PXRD) of crystalline form 1 of maraviroc phosphate is shown in FIG. 1.

According to another aspect of the present invention, there is provided a process for the preparation of crystalline form 1 of maraviroc phosphate, which comprises:
  a) providing a solution of maraviroc in a ketonic solvent, acetonitrile, an chlorinated solvent or mixture thereof;
  b) adding phosphoric acid to the solution obtained in step (a);
  c) slurrying the reaction mass obtained in step (b); and
  d) isolating crystalline form 1 of maraviroc phosphate.

The ketonic solvent used in step (a) may preferably be selected from acetone, methyl ethyl ketone, methyl isobutyl ketone and diethyl ketone, and more preferably the ketonic solvent is acetone.

The chlorinated solvent used in step (a) may preferably be selected from methylene chloride, chloroform, carbon tetrachloride and ethylene dichloride, and more preferably the chlorinated solvent is methylene chloride.

The step (c) may conveniently be carried out at room temperature.

Crystalline form 1 of maraviroc phosphate may be isolated in step (d) by the methods known such as filtration or centrifugation.

According to another aspect of the present invention, there is provided a pharmaceutical composition comprising crystalline form 1 of maraviroc phosphate and pharmaceutically acceptable excipients, and optionally other therapeutic ingredients. The crystalline form 1 may preferable be formulated into tablets, capsules, suspensions, dispersions, injectables and other pharmaceutical forms.

Figure 2:
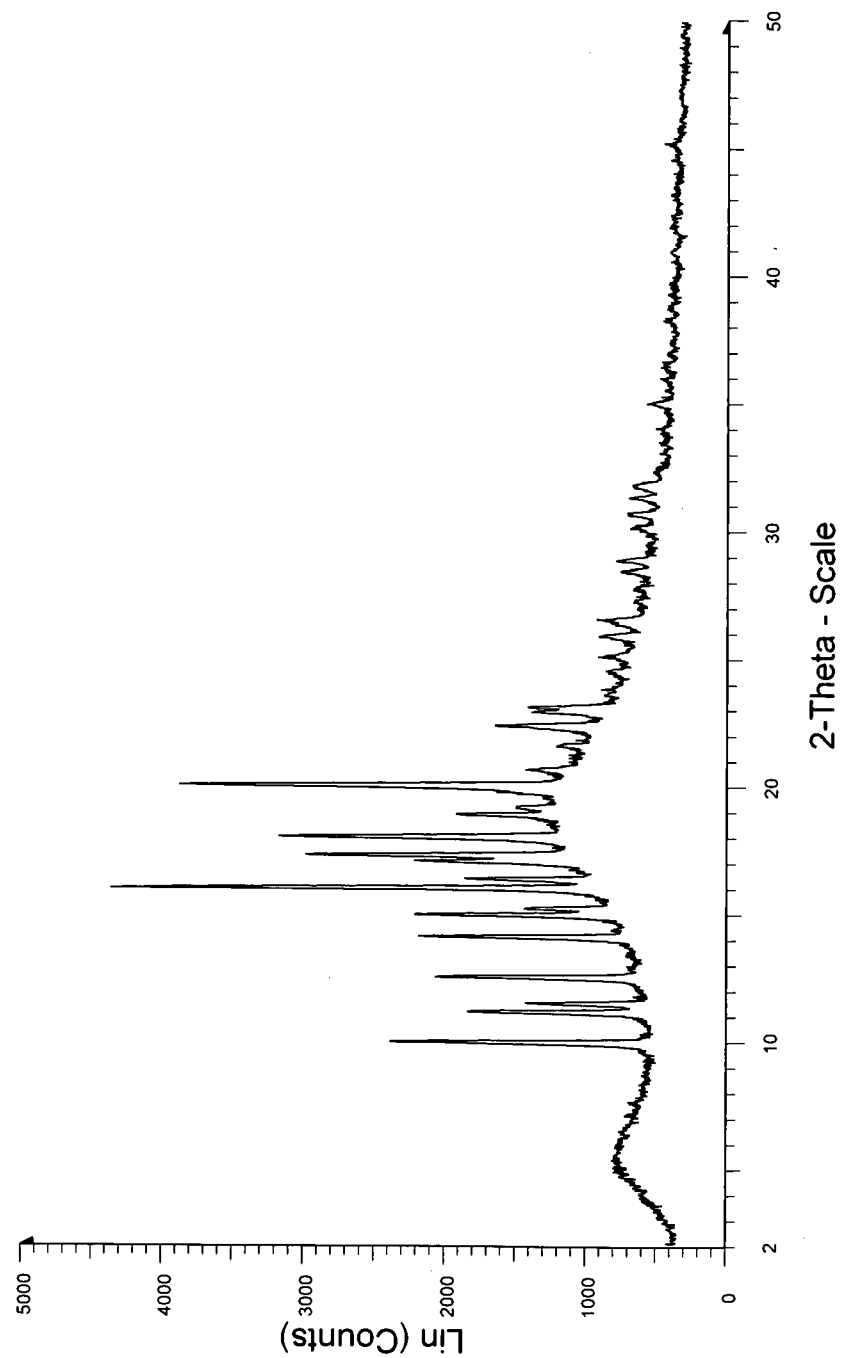
FIG. 2 is X-ray powder diffraction spectrum of crystalline form 2 of maraviroc phosphate.

According to another aspect of the present invention, there is provided a crystalline form of maraviroc phosphate designated as form 2 characterized by peaks in the powder x-ray diffraction spectrum having 2θ angle positions at about 9.9, 11.1, 12.5, 14.1, 15.0, 16.0, 17.1, 17.3, 18.0, 20.0 and 23.1±0.2 degrees. The powdered x-ray diffractogram of crystalline form 2 of maraviroc phosphate is shown in FIG. 2.

According to another aspect of the present invention, there is provided a process for the preparation of crystalline form 2 of maraviroc phosphate, which comprises:
 a) providing a solution of maraviroc in an ester solvent;
 b) adding phosphoric acid to the solution obtained in step (a);
 c) slurrying the reaction mass obtained in step (b); and
 d) isolating crystalline form 2 of maraviroc phosphate.

The ester solvent used in step (a) may preferably be a solvent or mixture of solvents selected from ethyl acetate, methyl acetate, isopropyl acetate, tert-butyl methyl acetate and ethyl formate, and more preferably the ester solvent is ethyl acetate.

The step (c) may conveniently be carried out at room temperature.

Crystalline form 2 of maraviroc phosphate may be isolated in step (d) by the methods known such as filtration or centrifugation.

According to another aspect of the present invention, there is provided a pharmaceutical composition comprising crystalline form 2 of maraviroc phosphate and pharmaceutically acceptable excipients and optionally other therapeutic ingredients. The crystalline form 2 may preferable be formulated into tablets, capsules, suspensions, dispersions, injectables and other pharmaceutical forms.

Figure 3:
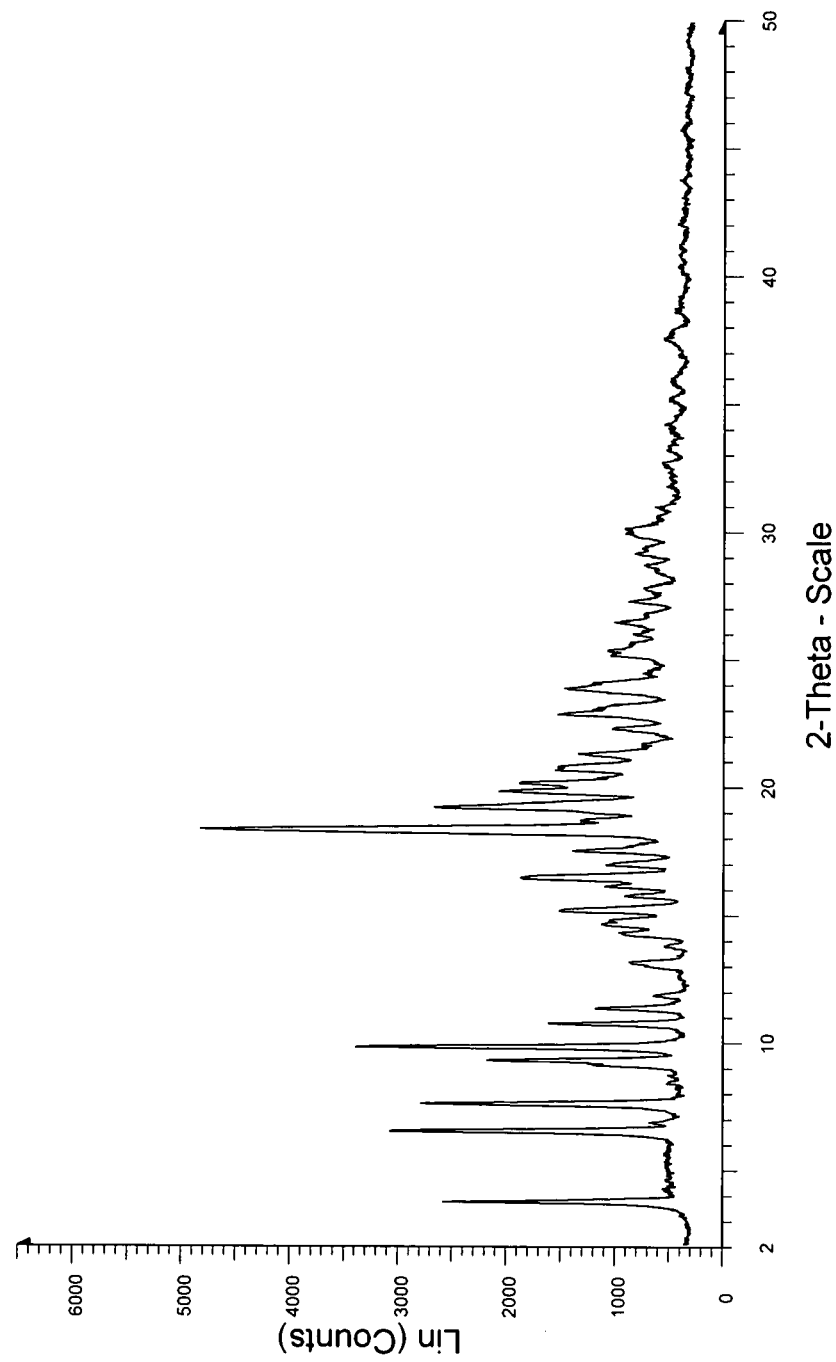
FIG. 3 is X-ray powder diffraction spectrum of crystalline form 3 of maraviroc phosphate.

According to another aspect of the present invention, there is provided a crystalline form of maraviroc phosphate designated as form 3 characterized by peaks in the powder x-ray diffraction spectrum having 2θ angle positions at about 3.7, 6.5, 7.5, 9.2, 9.8, 16.4, 18.3, 19.2, 19.8 and 22.6±0.2 degrees. The powdered x-ray diffractogram of crystalline form 3 of maraviroc phosphate is shown in FIG. 3.

According to another aspect of the present invention, there is provided a process for the preparation of crystalline form 3 of maraviroc phosphate, which comprises:
 a) providing a solution of maraviroc in isopropyl alcohol;
 b) adding phosphoric acid to the solution obtained in step (a);
 c) slurrying the reaction mass obtained in step (b); and
 d) isolating crystalline form 3 of maraviroc phosphate.

The step (c) may conveniently be carried out at room temperature.

Crystalline form 3 of maraviroc phosphate may be isolated in step (d) by the methods known such as filtration or centrifugation.

According to another aspect of the present invention, there is provided a pharmaceutical composition comprising crystalline form 3 of maraviroc phosphate and pharmaceutically acceptable excipients, and optionally other therapeutic ingredients. The crystalline form 3 may preferable be formulated into tablets, capsules, suspensions, dispersions, injectables and other pharmaceutical forms.

Figure 4:
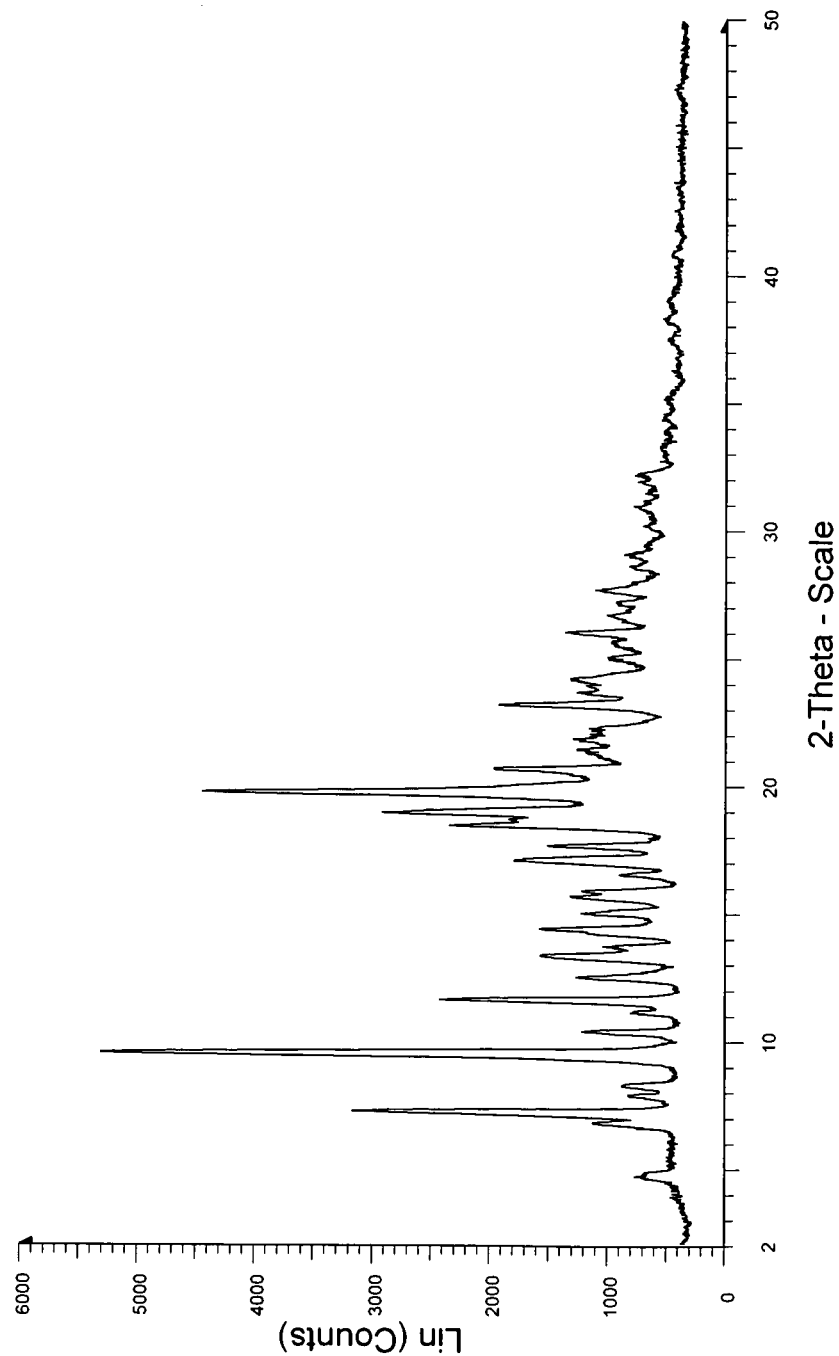
FIG. 4 is X-ray powder diffraction spectrum of crystalline form 4 of maraviroc phosphate.
Figure 5:
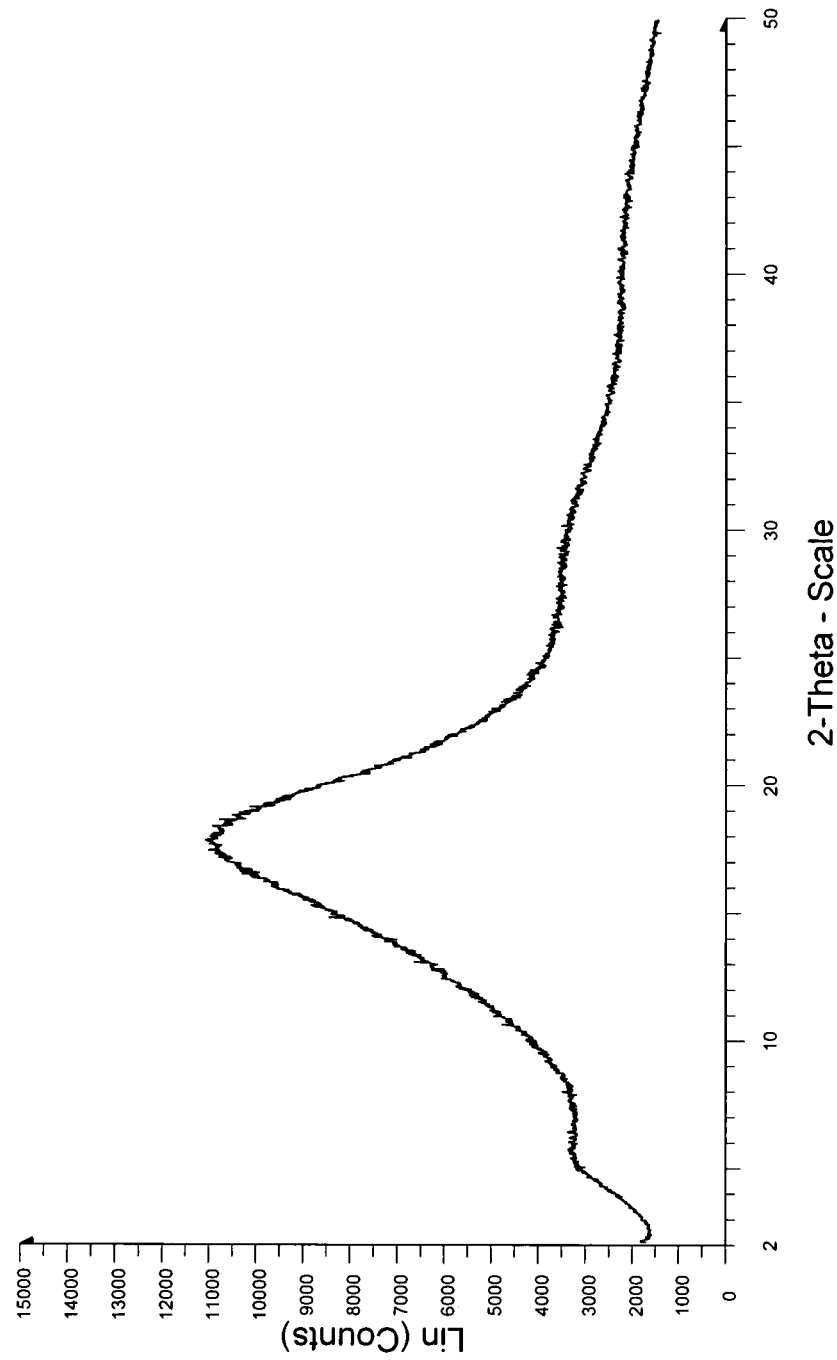
FIG. 5 is X-ray powder diffraction spectrum of maraviroc amorphous form.

According to another aspect of the present invention, there is provided a crystalline form of maraviroc phosphate designated as form 4 characterized by peaks in the powder x-ray diffraction spectrum having 2θ angle positions at about 7.2, 9.5, 11.6, 18.4, 18.9, 19.7 and 23.2±0.2 degrees. The powdered x-ray diffractogram of crystalline form 4 of maraviroc phosphate is shown in FIG. 4.

According to another aspect of the present invention, there is provided a process for the preparation of crystalline form 4 of maraviroc phosphate, which comprises:
 a) providing a solution of maraviroc in ethanol;
 b) adding phosphoric acid to the solution obtained in step (a);
 c) slurrying the reaction mass obtained in step (b) at below 20° C.; and
 d) isolating crystalline form 4 of maraviroc phosphate.

The step (c) may preferably be carried out at below 10° C. and more preferably at about 0 to 5° C.

Crystalline form 4 of maraviroc phosphate may be isolated in step (d) by the methods known such as filtration or centrifugation.

According to another aspect of the present invention, there is provided a pharmaceutical composition comprising crystalline form 4 of maraviroc phosphate and pharmaceutically acceptable excipients, and optionally other therapeutic ingredients. The crystalline form 4 may preferable be formulated into tablets, capsules, suspensions, dispersions, injectables and other pharmaceutical forms.

According to another aspect of the present invention, there is provided a process for the preparation of maraviroc amorphous form, which comprises:
 a) dissolving an acid addition salt of maraviroc in water;
 b) adjusting the pH of the reaction mass to about 7.0 to 9.0 with a base;
 c) extracting maraviroc into organic solvent;
 d) removing the solvent from the solution obtained in step (c) to obtain a residual mass;
 e) slurrying the residual mass obtained in step (d) with aliphatic hydrocarbon solvent or aromatic solvent; and
 f) isolating maraviroc amorphous form.

Preferably the acid addition salt of maraviroc used in step (a) is phosphate salt of maraviroc.

Preferably the pH of the reaction mass in step (b) may be adjusted to 7.5-8.6 and more preferably the pH is adjusted to 8.0-8.5.

The base used in step (b) may preferably be an organic base or an inorganic base selected from ammonium, sodium hydroxide and potassium hydroxide, and more preferably the base is ammonia.

The organic solvent used in step (c) may preferably be a solvent or mixture of solvents selected from the group consisting of a chlorinated solvent, an ester solvent, a ketonic solvent and an ether solvent.

Preferably the chlorinated solvent may be selected from methylene chloride, chloroform, carbon tetrachloride and ethylene dichloride, and more preferably the chlorinated solvent is methylene chloride.

Preferably the ester solvent may be selected from ethyl acetate, methyl acetate, isopropyl acetate, tert-butyl methyl acetate and ethyl formate, and more preferably the ester solvent is ethyl ester.

The ketonic solvent may preferably be selected from methyl ethyl ketone, methyl isobutyl ketone and diethyl ketone, and more preferably the ketonic solvent is methyl isobutyl ketone.

The ether solvent may preferably be selected from tetrahydrofuran, 1,4-dioxane, methyl tert-butyl ether, diisopropyl ether and diethyl ether, and more preferably the ether solvents are methyl tert-butyl ether and diisopropyl ether.

The step (a), (b) and (c) may be performed simultaneously by dissolving the acid addition salt of maraviroc in the mixture of water and the organic solvent to obtain a biphasic system, followed by separating the aqueous layer and collecting the organic layer.

Removal of the solvent may be carried out in step (d) at atmospheric pressure or at reduced pressure. Removal of the solvent may preferably be carried out until the solvent is almost completely distilled off.

The aliphatic hydrocarbon solvent or aromatic solvent used in step (e) may preferably be a solvent or a mixture of solvents selected from cyclohexane, hexane, n-heptane, toluene, xylene and benzene. More preferably the aliphatic hydrocarbon solvents are cyclohexane, hexane and n-heptane, still more preferably the aliphatic hydrocarbon solvent is cyclohexane.

Maraviroc amorphous form may be isolated in step (f) by the methods known such as filtration or centrifugation.

According to another aspect of the present invention, there is provided a pharmaceutical composition comprising maraviroc amorphous form and pharmaceutically acceptable excipients, and optionally other therapeutic ingredients. The amorphous form of maraviroc may preferable be formulated into tablets, capsules, suspensions, dispersions, injectables and other pharmaceutical forms.

Maraviroc used in the present invention can be prepared by the known process, for example, by a) reacting 4,4-difluoro cyclohexane carboxylic acid with thionyl chloride in an organic solvent;
b) heating the reaction mass obtained in step (a) at about 90° C. to obtain acid chloride compound;
c) reacting (S)-3-(3-(3-isopropyl-5-methyl-4H-1,2,4-triazol-4-yl)-8-azabicyclo[3.2.1]octan-8-yl)-1-phenylpropylcarbamate with acid chloride compound obtained in step (b) in the presence of potassium carbonate or cesium carbonate in an chlorinated solvent or acetonitrile;
d) maintaining the reaction mass obtained in step (c) at below 35° C.; and
e) isolating maraviroc.

The organic solvent used in step (a) may preferably be a solvent or mixture of solvents selected from toluene, benzene, xylene, hexane, cyclohexane and heptanes, and more preferably the organic solvent is toluene.

The chlorinated solvent used in step (c) may preferably be a solvent or mixture of solvents selected from methylene chloride, ethylene chloride, chloroform and carbon tetrachloride. More preferably the chlorinated solvent is methylene chloride.

The reaction mass may preferably be maintained in step (d) at about 25 to 35° C.

Maraviroc may be isolated in step (e) by the methods known such as filtration or centrifugation.

The invention will now be further described by the following examples, which are illustrative rather than limiting.

EXAMPLES

Example 1

Preparation of tert-butyl (1S)-3-oxo-1-phenylpropylcarbamate

Step-I: Preparation of tert-butyl (3S)-2-(methoxycarbonyl)-1-phenylethylcarbamate Sodium carbonate (59 gm) was added to water (225 ml) for 5 minutes and then cooled to 0 to 5° C. Methanol (200 ml) and methyl (3S)-3-amino-3-phenylpropanoate (50 gm) as obtained in example 1 were added to the solution. To the reaction mass was added boc-anhydride (71 gm) and methanol (250 ml), and maintained for 30 minutes at 0 to 5° C. The reaction mass was further maintained for 1 hour 30 minutes at room temperature. Water (500 ml) was added to the reaction mass and then the layers were separated. The aqueous layer was extracted with ethyl acetate. The combined organic layer was dried with sodium sulphate and the solvents were distilled off under vacuum to obtain a residual mass. To the residual mass was added hexane (100 ml) and stirred for 1 hour, filtered. The solid obtained was dried to obtain 74 gm of tert-butyl (3S)-2-(methoxycarbonyl)-1-phenylethylcarbamate.

Step-II: Preparation of tert-butyl (1S)-3-hydroxy-1-phenylpropylcarbamate

Lithium aluminum hydride (2 gm) was added to tetrahydrofuran (50 ml) under nitrogen atmosphere and then cooled to 0 to 5° C. To the solution was added a solution of tert-butyl (3S)-2-(methoxycarbonyl)-1-phenylethyl carbamate (10 gm) as obtained in step-I in tetrahydrofuran (30 ml) and maintained for 30 minutes at 5 to 10° C. The reaction mass was quenched with ice water (20 ml) and the reaction mass was filtered through hyflow bed. The layers were separated and the aqueous layer was extracted with ethyl acetate. The combined organic layer was dried with sodium sulphate and concentrated the tetrahydrofuran solvent to obtain 8.7 gm of tert-butyl (1S)-3-hydroxy-1-phenylpropylcarbamate.

Step-III: Preparation of tert-butyl (1S)-3-oxo-1-phenylpropylcarbamate

Tert-butyl (1S)-3-hydroxy-1-phenylpropylcarbamate (10 gm) as obtained in step-II was added to methylene chloride (80 ml) at room temperature. The mixture was cooled to 0 to 5° C. and then added sodium bromide (4.5 gm) and sodium carbonate (8 gm). 2,2,6,6-Tetramethylpiperidine-1-oxyl (0.06 gm) was added to the reaction mass under nitrogen atmosphere and then added sodium hypochlorite (109 ml; 4%) slowly at 0 to 5° C. The reaction mass was maintained for 2 hours at room temperature and then added sodium thiosulphate solution (15 ml; 10%). The separated aqueous layer was extracted with methylene chloride. The combined organic layer was dried with sodium sulphate and methylene chloride solvent was distilled off under vacuum to obtain a crude solid. To the crude solid was dissolved in hexane (30 ml) and stirred for 1 hour 30 minutes, filtered. The solid obtained was dried to obtain 8.5 gm of tert-butyl (1S)-3-oxo-1-phenylpropylcarbamate.

Example 2

Preparation of 3-(3-isopropyl-5-methyl-4H-1,2,4-triazol-4-yl)-exo-8-aza-bicyclo[3.2.1]octane Step-I: Preparation of 8-benzyl-8-azabicyclo[3.2.1]octan-3-one oxime Sodium hydroxide (74 gm) was added to water (150 ml) at reflux under stirring. Nortropinone hydrochloride (100 gm) was added to the solution and stirred for 20 minutes, and then added benzyl chloride (94 gm) and tetrahydrofuran (300 ml). The contents were heated to reflux and maintained for 15 hours at reflux. The contents were cooled to room temperature and then added hydroxylamine hydrochloride (72 gm) at room temperature. The contents were maintained for 3 hours at room temperature and then added water (200 ml). Sodium hydroxide solution (40%, 50 ml) was added to the reaction mass and then the layers were separated. The aqueous layer was extracted with ethyl acetate and the combined organic layer was dried with sodium sulphate to obtain a crude solid. The crude solid was dissolved in n-hexane (300 ml) and stirred for 1 hour. The separated solid was filtered and dried to obtain 134 gm of 8-benzyl-8-azabicyclo[3.2.1]octan-3-one oxime.

Step-II: Preparation of 8-benzyl-8-azabicyclo[3.2.1]octan-3-exo-amine

8-Benzyl-8-azabicyclo[3.2.1]octan-3-one oxime (50 gm) as obtained in step-I was added to isopentanol (750 ml) and then heated to reflux. Sodium metal (61 gm) was added slowly to the reaction mass and maintained for 2 hours at reflux. The reaction mass was cooled to 0° C. and then added water (200 ml) and hydrochloride (6N, 600 ml). The organic layer was separated and extracted with hydrochloride. The combined aqueous layer was basified with sodium hydroxide (40%, 200 ml). The aqueous solution was extracted with methylene chloride and the combined organic layer was dried with sodium sulfate. The solvent was distilled off under vacuum to obtain 42 gm of 8-benzyl-8-azabicyclo[3.2.1]octan-3-exo-amine.

Step-III: Preparation of N-(8-benzyl-8-azabicyclo[3.2.1]octan-3yl)isobutyramide Water (350 ml), potassium carbonate (48 gm), methylene chloride (250 ml) and 8-benzyl-8-azabicyclo[3.2.1]octan-3-exo-amine (50 gm) as obtained in step-II were added and then cooled to 0 to 5° C. Isobutyryl chloride (30 gm) was added slowly to the reaction mass at 0 to 5° C. The contents were maintained for 1 hour at 0 to 5° C. and the reaction mass allowed to room temperature. The reaction mass was maintained for 11 hours at room temperature and then the layers were separated. The aqueous layer was extracted with methylene chloride and the combined organic layer was dried with sodium sulfate. Ethyl acetate (300 ml) was added to the organic layer and heated to reflux. The reaction mass was maintained for 1 hour at reflux. The reaction mass was cooled to 0 to 5° C. and stirred for 2 hours at 0 to 5° C. The separated solid was filtered and dried to obtain 50.5 gm of N-(8-benzyl-8-azabicyclo[3.2.1]octan-3yl)isobutyramide.

Step-IV: Preparation of N'-acetyl-N-(8-benzyl-8-azabicyclo[3.2.1]octan-3yl) isobutyroydrazonamide Methylene chloride (250 ml) was added to phosphorus pentachloride (54 gm) and then cooled to 0° C. A solution of N-(8-benzyl-8-azabicyclo[3.2.1]octan-3-yl)isobutyramide (50 gm) as obtained in step-III in methylene chloride (250 ml) was slowly added to the solution at 0 to 5° C. The reaction mass maintained for 30 minutes at 0 to 5° C., and the reaction mass allowed to room temperature and maintained for 2 hours. A solution of acetic hydrazide (26 gm) in acetonitrile (250 ml) was added to reaction mass and then heated to reflux. The reaction mass was maintained for 2 hours at reflux and the solvents were distilled off under vacuum at below 50° C. to obtain a residual mass. The residual mass was cooled to 5° C. and then added water (100 ml). The pH of the reaction mass was adjusted to 10 with sodium hydroxide solution (10%, 450 ml) at below 25° C. and then the layers were separated. The aqueous layer was extracted with methylene chloride. The total organic layer was dried with sodium sulfate and concentrated the solvent to obtain 60 gm of N'-acetyl-N-(8-benzyl-8-azabicyclo[3.2.1]octan-3 yl)isobutyroydrazonamide.

Step-V: Preparation of 8-benzyl-3-(3-isopropyl-5-methyl-4H-1,2,4-triazol-4-yl)-exo-8-azabicyclo[3.2.1]octane N'-Acetyl-N-(8-benzyl-8-azabicyclo[3.2.1]octan-3yl) isobutyroydrazonamide (60 gm) as obtained in step-IV was dissolved in acetonitrile (150 ml) and then added acetic acid (9 ml). The contents were heated to reflux and maintained for 2 hours at reflux. The solvent was distilled off under vacuum to obtain a residual mass. To the residual mass was added methylene chloride (150 ml) and water (100 ml), and pH of the reaction mass was adjusted to 10 with sodium hydroxide solution (10%, 150 ml). The separated aqueous layer was extracted with methylene chloride (150 ml) and the total organic layer was dried with sodium sulphate to obtain a residue. To the residue was added n-hexane (200 ml) and heated to reflux. The reaction mass was maintained for 30 minutes at reflux. The reaction mass was cooled to room temperature and stirred for 1 hour at room temperature, filtered. The solid obtained was dried to obtain 43.1 gm of 8-benzyl-3-(3-isopropyl-5-methyl-4H-1,2,4-triazol-4-yl)-exo-8-azabicyclo[3.2.1]octane.

Step-VI: Preparation of 3-(3-isopropyl-5-methyl-4H-1,2,4-triazol-4-yl)-exo-8-azabicyclo[3.2.1]octane 8-Benzyl-3-(3-isopropyl-5-methyl-4H-1,2,4-triazol-4-yl)-exo-8-azabicyclo[3.2.1]octane (100 gm) as obtained in step-V was dissolved in ethanol (1000 ml) and then added ammonium formate (194 gm) and palladium carbon (25 gm). The contents were heated to reflux and maintained for 2 hours at reflux. Ammonium solution (60 ml) was added to reaction mass and maintained for 1 hour at reflux. The reaction mass was filtered through high flow bed and the solvent was distilled off under vacuum at below 50° C. to obtain a residual mass. The residual mass was dissolved in ethyl acetate (400 ml) and heated to reflux. The reaction mass was stirred for 40 minutes at reflux and filtered. The solid obtained was dried to obtain 65 gm of 3-(3-isopropyl-5-methyl-4H-1,2,4-triazol-4-yl)-exo-8-azabicyclo[3.2.1]octane.

Example 3

Preparation of Maraviroc

Step-I: Preparation of ten-butyl (1S)-3-(3-(3-isopropyl-5-methyl-4H-1,2,4-triazol-4-yl)-8-azabicyclo[3.2.1]octan-8-O-1-phenylpropylcarbamate Sodium triacetoxyborohydride (126 gm) was dissolved in methanol (350 ml) at 0 to 5° C. to obtain a solution. A solution of 3-(3-isopropyl-5-methyl-4H-1,2,4-triazol-4-yl)-exo-8-azabicyclo[3.2.1]octane (50 gm) as obtained in example 2 and tert-butyl (1S)-3-oxo-1-phenylpropylcarbamate (64 gm) as obtained example 1 in methanol (400 ml) was added to the solution at 0 to 5° C. To the reaction mass was added acetic acid (15 ml) at 0 to 5° C. and maintained for 15 minutes at 0 to 5° C. Then the reaction mass was allowed to room temperature and maintained for 5 hours at room temperature. The pH of the reaction mass was adjusted to 8.0 to 9.0 with sodium carbonate solution (20%, 250 ml) and extracted with methylene chloride. The organic layer was dried with sodium sulphate and concentrated the solvent to obtain 100 gm of tert-butyl (1S)-3-(3-(3-isopropyl-5-methyl-4H-1,2,4-triazol-4-yl)-8-azabicyclo-[3.2.1]octan-8-yl)-1-phenylpropylcarbamate.

Step-II: Preparation of (1S)-3-(3-(3-isopropyl-5-methyl-4H-1,2,4-triazol-4-yl)-8-azabicyclo[3.2.1]octan-8-O-1-phenylpropylcarbamate Tert-butyl (1S)-3-(3-(3-isopropyl-5-methyl-4H-1,2,4-triazol-4-yl)-8-azabicyclo-[3.2.1]octan-8-yl)-1-phenylpropylcarbamate (18 gm) as obtained in step-I was dissolved in methanol (108 ml) and then added hydrochloric acid (3N, 108 ml). The contents were heated to reflux and maintained for 2 hours at reflux. The methanol solvent was distilled off under vacuum at below 50° C. to obtain a residual mass. The residual mass was treated with carbon (1.8 gm) and stirred for 30 minutes. The reaction mass was filtered through hyflow bed and pH of the reaction mass was adjusted to 9.0 with saturated sodium carbonate solution (108 ml). The reaction mass was extracted with methylene chloride and the organic layer was dried with sodium sulphate. The solvent was distilled off under vacuum to obtain 11 gm of (1S)-3-(3-(3-isopropyl-5-methyl-4H-1,2,4-triazol-4-yl)-8-azabicyclo[3.2.1]octan-8-yl)-1-phenyl-propylcarbamate.

Step-III: Preparation of N-{(S)-3-[3-(3-isopropyl-5-methyl-4H-1,2,4-triazol-4-yl)-8-azabicyclo-[3.2.1]octan-8-yl]-1-phenylpropyl}-4,4-difluorocyclohexanecarboxamide (maraviroc)

4,4-Difluorocyclohexanecarboxylic acid (39 gm) was dissolved in toluene (460 ml) and then added thionyl chloride (101 ml). The contents were heated to reflux and maintained for 2 hours at reflux. The reaction mass was cooled to room temperature and the solvent was distilled off under vacuum to obtained a residual mass. Potassium carbonate (80 gm) was added to water (438 ml) and stirred for 20 minutes at room temperature. The solution was cooled to 0 to 5° C. and then added (1S)-3-(3-(3-isopropyl-5-methyl-4H-1,2,4-triazol-4-yl)-8-azabicyclo[3.2.1]octan-8-yl)-1-phenylpropyl-carbamate (73 gm) as obtained in step-II in methylene chloride (219 ml). To the reaction mass was added residual mass as obtained above in methylene chloride (510 ml) and maintained for 2 hours at room temperature. The layers were separated and the aqueous layer was extracted with methylene chloride. The combined organic layer was treated with carbon (7 gm) and stirred for 30 minutes. The reaction mass was filtered through hyflow bed and dried with sodium sulfate. The solvent was distilled off under vacuum to obtain residual mass. To the residual mass was added ethyl acetate (290 ml) and heated to reflux. The reaction mass was stirred for 45 minutes at reflux and then cooled to room temperature. The reaction mass was stirred for 3 hours and filtered. The solid obtained was dried to obtain 74 gm of maraviroc.

Example 4

Preparation of Maraviroc

Example 3 (step-III) was repeated using cesium carbonate instead of potassium carbonate to obtain maraviroc.

Example 5

Preparation of Maraviroc Phosphate 4,4-Difluorocyclohexanecarboxylic acid (30 gm) was dissolved in toluene (75 ml) and dimethylformamide (2 ml) and then added thionyl chloride (66.4 ml). The contents were heated to reflux and maintained for 3 hours at reflux. The solvent was distilled off under vacuum at below 55° C. to obtain a residual mass. The residual mass was dissolved in toluene (50 ml) to obtain acid chloride solution. (1S)-3-(3-(3-Isopropyl-5-methyl-4H-1,2,4-triazol-4-yl)-8-azabicyclo[3.2.1]octan-8-yl)-1-phenylpropylcarbamate (42 gm), methylene chloride (640 ml), tetra butyl ammonium bromide (1 gm), dimethylamino pyridine (1 gm), saturated sodium carbonate solution (780 ml) and water (660 ml) were added and then cooled to 10° C. To the reaction mass was added a solution of acid chloride obtained above for 30 minutes and stirred for 45 minutes at 10 to 15° C. The layers were separated and the aqueous layer was extracted with dichloromethane. The combined organic layer was dried with sodium sulfate and treated with carbon. The solvent was distilled off under vacuum at below 45° C. to obtain residual mass. To the residue was dissolved in acetone (400 ml) and stirred for 30 minutes at room temperature to obtain a solution. To the solution was added phosphoric acid (11 gm) and stirred for 11 hours at room temperature. The solid obtained was collected by filtration and dried to obtain 60 gm of maraviroc phosphate.

Example 6

Preparation of Crystalline Form 1 of Maraviroc Phosphate

Maraviroc (50 gm) was dissolved in acetone (400 ml) and stirred for 30 minutes at room temperature to obtain a solution. To the solution was added phosphoric acid (11 gm) and stirred for 11 hours at room temperature. The solid obtained was collected by filtration and dried to obtain 55 gm of crystalline form 1 of maraviroc phosphate.

Example 7

Preparation of Crystalline Form 1 of Maraviroc Phosphate

Maraviroc (10 gm) was dissolved in methylene chloride (100 ml) and stirred for 30 minutes at room temperature. To the solution was added phosphoric acid (2 gm) and stirred for 11 hours at room temperature. The solid obtained was collected by filtration and dried to obtain 11 gm of crystalline form 1 of maraviroc phosphate.

Example 8

Preparation of Crystalline Form 1 of Maraviroc Phosphate

Maraviroc (10 gm) was dissolved in acetonitrile (100 ml) and stirred for 30 minutes at room temperature. To the solution was added phosphoric acid (2 gm) and stirred for 11 hours at room temperature, filtered. The solid obtained was dried to obtain 11 gm of crystalline form 1 of maraviroc phosphate.

Example 9

Preparation of Crystalline Form 1 of Maraviroc Phosphate

Maraviroc (10 gm) was dissolved in methyl ethyl ketone (100 ml) and stirred for 30 minutes at room temperature. To the solution was added phosphoric acid (2 gm) and stirred for 11 hours at room temperature. The solid obtained was collected by filtration and dried to obtain 10 gm of crystalline form 1 of maraviroc phosphate.

Example 10

Preparation of Crystalline Form 2 of Maraviroc Phosphate

Maraviroc (10 gm) was dissolved in ethyl acetate (100 ml) and stirred for 30 minutes at room temperature. To the solution was added phosphoric acid (2 gm) and stirred for 11 hours at room temperature, filtered. The solid obtained was dried to obtain 11 gm of crystalline form 2 of maraviroc phosphate.

Example 11

Preparation of Crystalline Form 3 of Maraviroc Phosphate

Maraviroc (10 gm) was dissolved in isopropyl alcohol (100 ml) and stirred for 30 minutes at room temperature. To the solution was added phosphoric acid (2 gm) and stirred for 11 hours at room temperature. The solid obtained was collected by filtration and dried to obtain 10.5 gm of crystalline form 3 of maraviroc phosphate.

Example 12

Preparation of Crystalline Form 4 of Maraviroc Phosphate

Maraviroc (10 gm) was dissolved in ethanol (900 ml), and stirred for 30 minutes at room temperature. To the solution was added phosphoric acid (20 gm) and then cooled to 0 to 5° C. The reaction mass was stirred for 11 hours at 0 to 5° C. and filtered. The solid obtained was dried to obtain 10 gm of crystalline form 4 of maraviroc phosphate.

Example 13

Preparation of Crystalline Form 4 of Maraviroc Phosphate

Maraviroc (100 gm) was dissolved in ethanol (100 ml) and stirred for 30 minutes at room temperature. To the solution was added phosphoric acid (2 gm) and then cooled to 0 to 5° C. The reaction mass was stirred for 12 hours at 0 to 5° C. and filtered. The solid obtained was dried to obtain 98 gm of crystalline form 4 of maraviroc phosphate.

Example 14

Preparation of Maraviroc Amorphous Form

Maraviroc phosphate (60 gm) as obtained in example 5 was dissolved in methylene chloride (500 ml) and water (400 ml). The pH of the reaction mass was adjusted to 8.0 to 8.5 with ammonia solution (30 ml) and stirred for 15 minutes. The layers were separated and the organic layer was dried with sodium sulfate and treated with carbon. The methylene chloride was distilled off under vacuum at below 45° C. to obtain residual mass. To the residual mass was added cyclohexane (400 ml) and stirred for 15 minutes at room temperature, filtered. The solid obtained was dried under vacuum at 85° C. for 13 hours to obtain 48 gm of maraviroc amorphous form (HPLC Purity: 99.96%).

Example 15

Preparation of Maraviroc Amorphous Form

Maraviroc phosphate (60 gm) was dissolved in water (400 ml) and pH of the reaction mass was adjusted to 8.0 to 8.5 with ammonia solution (30 ml). The layers were separated and the aqueous layer was extracted with methylene chloride. The organic layer was dried with sodium sulfate and treated with carbon. The methylene chloride was distilled off under vacuum at below 45° C. to obtain residual mass. To the residual mass was added cyclohexane (400 ml) and stirred for 15 minutes at room temperature, filtered. The solid obtained was dried under vacuum at 85° C. for 12 hours to obtain 47 gm of maraviroc amorphous form (HPLC Purity: 99.95%).

Example 16

Preparation of Maraviroc Amorphous Form

Maraviroc phosphate (6 gm) was dissolved in methylene chloride (50 ml) and water (40 ml). The pH of the reaction mass was adjusted to 8.0 to 8.5 with ammonia solution (4 ml) and stirred for 15 minutes. The layers were separated and the organic layer was dried with sodium sulfate and treated with carbon. The methylene chloride was distilled off under vacuum at below 45° C. to obtain residual mass. To the residual mass was added hexane (40 ml) and stirred for 30 minutes at room temperature. The solid obtained was collected by filtration and dried to obtain 4.7 gm of maraviroc amorphous form (HPLC Purity: 99.95%).

Example 17

Preparation of Maraviroc Amorphous Form

Maraviroc phosphate (6 gm) was dissolved in methylene chloride (50 ml) and water (40 ml). The pH of the reaction mass was adjusted to 8.0 to 8.5 with ammonia solution (3 ml) and then the layers were separated. The organic layer was dried with sodium sulfate and treated with carbon. The methylene chloride was distilled off under vacuum at below 45° C. to obtain residual mass. To the residual mass was added n-heptane (40 ml) and stirred for 30 minutes at room temperature. The solid obtained was collected by filtration and dried to obtain 4.6 gm of maraviroc amorphous form (HPLC Purity: 99.96%).

Example 18

Preparation of Maraviroc Amorphous Form

Crystalline form 1 of maraviroc phosphate (5 gm) as obtained in example 6 was dissolved in methylene chloride (50 ml) and water (40 ml). The pH of the reaction mass was adjusted to 8.0 to 8.5 with ammonia solution (3 ml) and then the layers were separated. The organic layer was dried with sodium sulfate and treated with carbon. The methylene chloride was distilled off under vacuum at below 45° C. to obtain residual mass and then added cyclohexane (40 ml). The reaction mass was stirred for 20 minutes at room temperature and filtered. The solid obtained was dried to obtain 3.9 gm of maraviroc amorphous form.

Example 19

Preparation of Maraviroc Amorphous Form

Example 18 was repeated using crystalline form 2 of maraviroc phosphate instead of crystalline form 1 of maraviroc phosphate to obtain maraviroc amorphous form.

Example 20

Preparation of Maraviroc Amorphous Form

Example 18 was repeated using crystalline form 3 of maraviroc phosphate instead of crystalline form 1 of maraviroc phosphate to obtain maraviroc amorphous form.

Example 21

Preparation of Maraviroc Amorphous Form

Example 18 was repeated using crystalline form 4 of maraviroc phosphate instead of crystalline form 1 of maraviroc phosphate to obtain maraviroc amorphous form.

Example 22

Preparation of Maraviroc Amorphous Form

Crystalline form 1 of maraviroc phosphate (5 gm) was dissolved in ethyl acetate (60 ml) and water (40 ml). The pH of the reaction mass was adjusted to 8.0 to 8.5 with ammonia solution (3 ml) and stirred for 15 minutes. The separated organic layer was dried with sodium sulfate and treated with carbon. The ethyl acetate was distilled off under vacuum at below 45° C. to obtain residual mass. To the residual mass was added cyclohexane (50 ml) and stirred for 15 minutes at room temperature, filtered. The solid obtained was dried to obtain 3.5 gm of maraviroc amorphous form.

Example 23

Preparation of Maraviroc Amorphous Form

Example 22 was repeated using crystalline form 2 of maraviroc phosphate instead of crystalline form 1 of maraviroc phosphate to obtain maraviroc amorphous form.

Example 24

Preparation of Maraviroc Amorphous Form

Example 22 was repeated using crystalline form 3 of maraviroc phosphate instead of crystalline form 1 of maraviroc phosphate to obtain maraviroc amorphous form.

Example 25

Preparation of Maraviroc Amorphous Form

Example 22 was repeated using crystalline form 4 of maraviroc phosphate instead of crystalline form 1 of maraviroc phosphate to obtain maraviroc amorphous form.

Example 26

Preparation of Maraviroc Amorphous Form

Crystalline form 1 of maraviroc phosphate (5 gm) was dissolved in methyl tert-butyl ether (60 ml) and water (40 ml). The pH of the reaction mass was adjusted to 8.0 to 8.5 with ammonia solution (3 ml) and stirred for 15 minutes. The separated organic layer was dried with sodium sulfate and treated with carbon. The methyl tert-butyl ether was distilled off under vacuum at below 45° C. to obtain residual mass. To the residual mass was added cyclohexane (50 ml) and stirred for 20 minutes at room temperature, filtered. The solid obtained was dried to obtain 3.4 gm of maraviroc amorphous form.

Example 27

Preparation of Maraviroc Amorphous Form

Example 26 was repeated using crystalline form 2 of maraviroc phosphate instead of crystalline form 1 of maraviroc phosphate to obtain maraviroc amorphous form.

Example 28

Preparation of Maraviroc Amorphous Form

Example 26 was repeated using crystalline form 3 of maraviroc phosphate instead of crystalline form 1 of maraviroc phosphate to obtain maraviroc amorphous form.

Example 29

Preparation of Maraviroc Amorphous Form

Example 26 was repeated using crystalline form 4 of maraviroc phosphate instead of crystalline form 1 of maraviroc phosphate to obtain maraviroc amorphous form.

Example 30

Preparation of Maraviroc Amorphous Form

Crystalline form 1 of maraviroc phosphate (5 gm) was dissolved in diisopropyl ether (60 ml) and water (40 ml). The pH of the reaction mass was adjusted to 8.0 to 8.5 with ammonia solution (3 ml) and stirred for 15 minutes. The separated organic layer was dried with sodium sulfate and treated with carbon. The diisopropyl ether was distilled off under vacuum at below 45° C. to obtain residual mass. To the residual mass was added cyclohexane (50 ml) and stirred for 20 minutes at room temperature, filtered. The solid obtained was dried to obtain 3.4 gm of maraviroc amorphous form.

Example 31

Preparation of Maraviroc Amorphous Form

Example 30 was repeated using crystalline form 2 of maraviroc phosphate instead of crystalline form 1 of maraviroc phosphate to obtain maraviroc amorphous form.

Example 32

Preparation of Maraviroc Amorphous Form

Example 30 was repeated using crystalline form 3 of maraviroc phosphate instead of crystalline form 1 of maraviroc phosphate to obtain maraviroc amorphous form.

Example 33

Preparation of Maraviroc Amorphous Form

Example 30 was repeated using crystalline form 4 of maraviroc phosphate instead of crystalline form 1 of maraviroc phosphate to obtain maraviroc amorphous form.

Example 34

Preparation of Maraviroc Amorphous Form

Crystalline form 1 of maraviroc phosphate (5 gm) was dissolved in water (40 ml) and pH of the reaction mass was adjusted to 8.0 to 8.5 with ammonia solution (4 ml). The layers were separated and the aqueous layer was extracted with ethyl acetate. The organic layer was dried with sodium sulfate and treated with carbon. The ethyl acetate was distilled off under vacuum at below 45° C. to obtain residual mass. To the residual mass was added cyclohexane (400 ml) and stirred for 15 minutes at room temperature, filtered. The solid obtained was dried under vacuum at 85° C. for 12 hours to obtain 47 gm of maraviroc amorphous form.

We claim:

1. A crystalline form 1 of maraviroc phosphate which is characterized by peaks in the powder x-ray diffraction spectrum having 2θ angle positions at 8.4, 9.7, 11.4, 18.2 and 18.8±0.2 degrees.

2. The crystalline form 1 of maraviroc phosphate of claim 1, characterized by an x-ray powder diffractogram as shown in FIG. 1.

3. A process for the preparation of crystalline form 1 of maraviroc phosphate as claimed in claim 1, which comprises:
   a. providing a solution of maraviroc in a ketonic solvent, acetonitrile, an chlorinated solvent, or mixture thereof;
   b. adding phosphoric acid to the solution obtained in step (a) to produce a reaction mass;
   c. slurrying the reaction mass obtained in step (b) to produce a slurry; and
   d. isolating crystalline form 1 of maraviroc phosphate from the slurry.

4. The process according to claim 3, wherein the ketonic solvent used in step (a) is selected from acetone, methyl ethyl ketone, methyl isobutyl ketone and diethyl ketone.

5. The process according to claim 4, wherein the ketonic solvent is acetone.

6. The process according to claim 3, wherein the chlorinated solvent used in step (a) is selected from methylene chloride, chloroform, carbon tetrachloride and ethylene dichloride.

7. The process according to claim 6, wherein the chlorinated solvent is methylene chloride.

8. The process according to claim 3, wherein the step (c) is carried out at room temperature.

9. A crystalline form 2 of maraviroc phosphate which is characterized by peaks in the powder x-ray diffraction spectrum having 2θ angle positions at 9.9, 11.1, 12.5, 14.1, 15.0, 16.0, 17.1, 17.3, 18.0, 20.0 and 23.1±0.2 degrees.

10. The crystalline form 2 of maraviroc phosphate of claim 9, characterized by an x-ray powder diffractogram as shown in FIG. 2.

11. A process for the preparation of crystalline form 2 of maraviroc phosphate as claimed in claim 9, which comprises:
   a. providing a solution of maraviroc in an ester solvent;
   b. adding phosphoric acid to the solution obtained in step (a) to provide a reaction mass;
   c. slurrying the reaction mass obtained in step (b) to form a slurry; and
   d. isolating crystalline form 2 of maraviroc phosphate from the slurry.

12. The process according to claim 11, wherein the ester solvent used in step (a) is a solvent or mixture of solvents selected from ethyl acetate, methyl acetate, isopropyl acetate, tert-butyl methyl acetate and ethyl formate.

13. The process according to claim 12, wherein the ester solvent is ethyl acetate.

14. The process according to claim 11, wherein the step (c) is carried out at room temperature.

15. A crystalline form 3 of maraviroc phosphate which is characterized by peaks in the powder x-ray diffraction spectrum having 2θ angle positions at 3.7, 6.5, 7.5, 9.2, 9.8, 16.4, 18.3, 19.2, 19.8 and 22.6±0.2 degrees.

16. The crystalline form 3 of maraviroc phosphate of claim 15, characterized by an x-ray powder diffractogram as shown in FIG. 3.

17. A process for the preparation of crystalline form 3 of maraviroc phosphate as claimed in claim 15, which comprises:
   a. providing a solution of maraviroc in isopropyl alcohol;
   b. adding phosphoric acid to the solution obtained in step (a) to provide a reaction mass;
   c. slurrying the reaction mass obtained in step (b) to provide a slurry; and
   d. isolating crystalline form 3 of maraviroc phosphate from the slurry.

18. The process according to claim 17, wherein the step (c) is carried out at room temperature.

19. A crystalline form 4 of maraviroc phosphate which is characterized by peaks in the powder x-ray diffraction spectrum having 2θ angle positions at 7.2, 9.5, 11.6, 18.4, 18.9, 19.7 and 23.2±0.2 degrees.

20. The A crystalline form 4 of maraviroc phosphate of claim 19, characterized by an x-ray powder diffractogram as shown in FIG. 4.

21. A process for the preparation of crystalline form 4 of maraviroc phosphate as claimed in claim 19, which comprises:
   a. providing a solution of maraviroc in ethanol;
   b. adding phosphoric acid to the solution obtained in step (a) to provide a reaction mass;
   c. slurrying the reaction mass obtained in step (b) at below 20° C. to provide a slurry; and
   d. isolating crystalline form 4 of maraviroc phosphate from the slurry.

22. The process according to claim 21, wherein the step (c) is carried out at below 10° C.

23. The process according to claim 22, wherein the step (c) is carried out at about 0 to 5° C.

24. A process for the preparation of maraviroc amorphous form, which comprises:
   a. dissolving an acid addition salt of maraviroc in water;
   b. adjusting the pH of the reaction mass to 7.0 to 9.0 with a base;
   c. extracting maraviroc into an organic solvent;
   d. removing the organic solvent from the solution obtained in step (c) to obtain a residual mass;
   e. slurrying the residual mass obtained in step (d) with an aliphatic hydrocarbon solvent or an aromatic solvent to provide a slurry; and
   f. isolating maraviroc amorphous form from the slurry.

* * * * *